United States Patent [19]

Watt

[11] 4,414,472
[45] Nov. 8, 1983

[54] METHOD FOR DETERMINING THE SOLIDS WEIGHT FRACTION OF A SLURRY

[75] Inventor: John S. Watt, Heathcote, Australia

[73] Assignee: Austalian Atomic Energy Commission, New South Wales, Australia

[21] Appl. No.: 187,884

[22] Filed: Sep. 17, 1980

[30] Foreign Application Priority Data

Sep. 27, 1979 [AU] Australia .................. PE 0686

[51] Int. Cl.³ .................................. G01N 23/00
[52] U.S. Cl. ...................... 250/359.1; 378/46; 378/53; 378/88
[58] Field of Search ............... 250/358 R, 359, 360, 250/272, 273; 378/44, 45, 46, 53, 88

[56] References Cited

U.S. PATENT DOCUMENTS

| | | | |
|---|---|---|---|
| 3,532,883 | 10/1970 | Dresia et al. | 250/358 R |
| 3,748,473 | 7/1973 | Chen | 250/392 |
| 4,057,729 | 11/1977 | Hewitt | 250/390 |
| 4,090,074 | 5/1978 | Watt et al. | 250/358 R X |
| 4,278,882 | 7/1981 | Clayton et al. | 250/359 X |

Primary Examiner—Davis L. Willis
Attorney, Agent, or Firm—Ladas & Parry

[57] ABSTRACT

A method for determining the solids weight fraction of a slurry especially a coal slurry is described based on a measure of the concentration (wt/wt) of hydrogen in the slurry by neutron transmission or scatter. Accuracy of the method can be improved by combining the neutron measurement with a γ-ray transmission or scatter measurement, and further improved by including a measurement of X-ray scatter or transmission. In the last mentioned case the mineral matter content of the coal in the slurry can also be determined.

14 Claims, 3 Drawing Figures

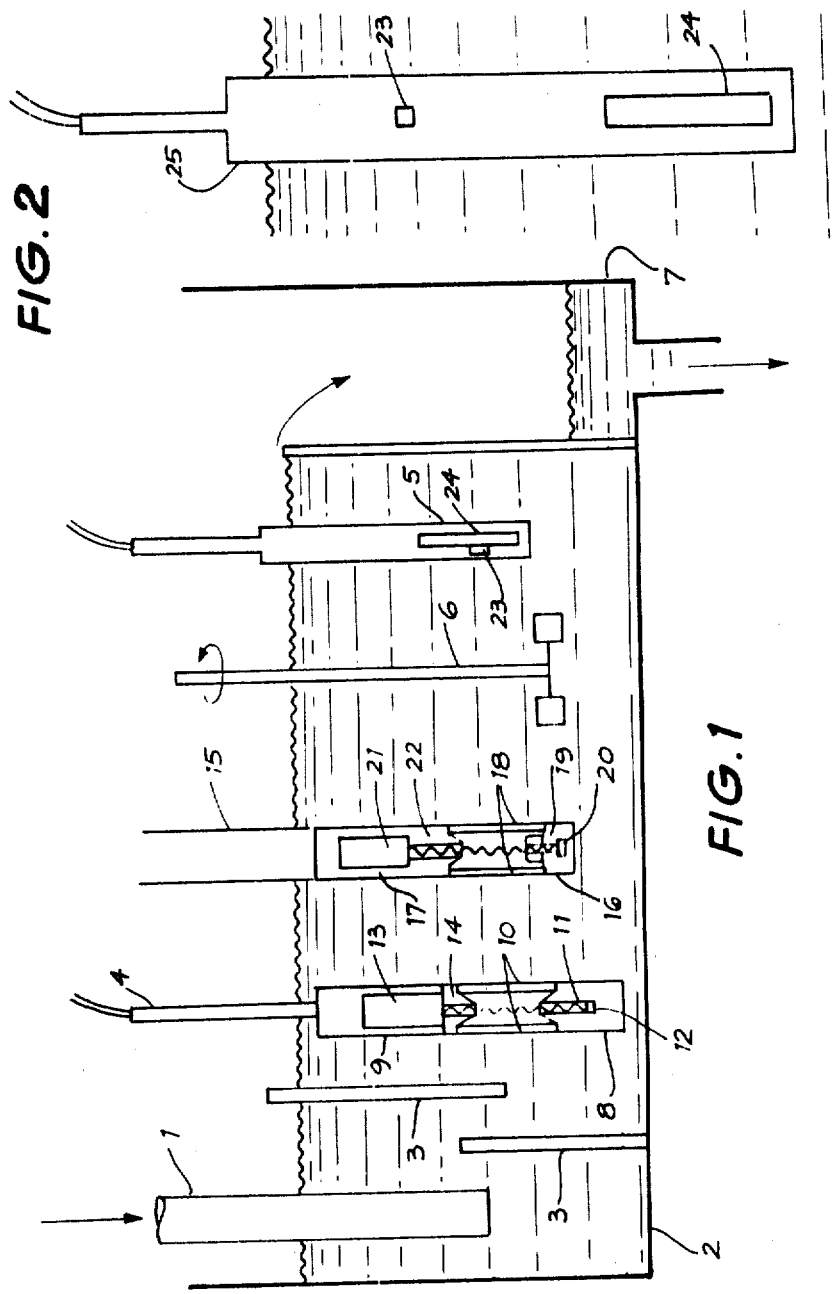

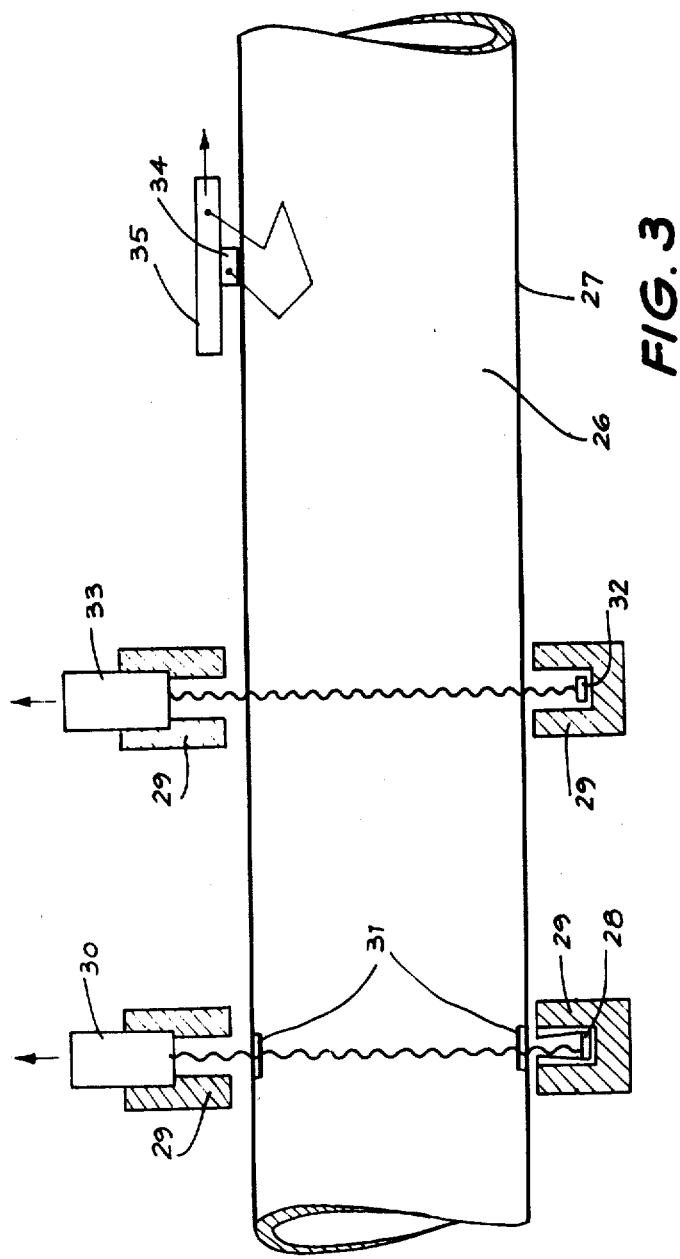

METHOD FOR DETERMINING THE SOLIDS WEIGHT FRACTION OF A SLURRY

The present invention relates to a method of determination of the solids weight fraction ($W_s$) of coal slurries and determination of the ash content of coal in coal slurries, based on determinations of the hydrogen content (wt./wt.) of the coal slurry and by a measure related to the concentration of the higher atomic number constituents (i.e. major constituents of the ash) of the coal slurry. The present invention is also applicable to the determination of the solids weight fraction of slurries, with solids other than coal, such as those resulting from alluvial tin mining operations. Although the invention is hereinbelow described by reference to its application to coal slurries, it should be understood that the method of the present invention has broader applications which are discussed hereinbelow where appropriate.

An accurate knowledge of the mass flow rate and ash content of coal in coal slurries is very important in many aspects of production or beneficiation of coal, and in transportation by pipeline of coal in slurries. This knowledge enables better control of these processes.

Coal consists of coal matter (oxygen and combustible materials, carbon, hydrogen and a little nitrogen and sulfur) and mineral matter (mainly of incombustible aluminium and other silicates, and a little iron sulfide which is partly combustible). Coal ash is the oxidised incombustible residue from the combustion of coal, and is closely correlated with the content of mineral water. A measure of mineral matter is thus also a measure of ash content. It is also indirectly a measure of coal matter and hence calorific value.

When coal is mixed with water to form a coal slurry, the solids weight fraction of a given volume of slurry is the weight of coal divided by the weight of coal and water.

Coal in slurries undergoes various stages of treatment in a coal washery to reduce the content of mineral matter and hence have an improved coal product. Coal is also transported by pipeline as a coal slurry. It is advantageous to have a continuous monitor of the mineral matter content of coal, and the solids weight fraction of the coal slurry, so that more efficient control of washeries and pipeline transportation can be achieved.

The usual way of determining the solids weight fraction of a slurry by continuous means is to measure the transmission of $\gamma$-rays through the slurry. Such a method is described by Carr-Brion K. G., "Performance of an on-stream radioisotope X-ray fluorescence analyzer" in Trans/Section C of Inst. Min. Metall. 76 C94-100 (1967), the disclosure of which is incorporated herein be reference. This method provides an accurate measure of solids weight fraction of coal slurries only if voidage (due to air entrained in the slurry) is very low e.g. less than approximately 0.001 cc of voids per cc slurry.

In many coal slurries, particularly coal flotation slurries, entrained air causes considerable voidage and interferes with the accuracy of determination of solids weight fraction and mineral matter content. This problem is discussed by Lyman G. J., "On line ash sensing in coal flotation slurries", North Queensland Conference 1978 of the Australasian Institute of Mining and Metallurgy, pages 245-255, the disclosure of which is incorporated herein by reference. In this method, the coal slurry is pressurised to about 300 psi in a sample by-line hence collapsing the entrained air. $\gamma$-ray and X-ray transmission measurements are made on the sample by line. However, this technique for collapsing voids adds considerable complexity to the measurement of solids weight fraction and mineral matter content.

The method of the present invention determines solids weight fraction and mineral matter content of coal slurries when entrained air and hence voidage is present or absent, and can be based on measurements made by probes immersed directly into plant slurry streams or mounted directly onto slurry pipelnes hence avoiding the need for slurry sample by-lines. Voidage of the coal slurry can also be determined by this method.

The present invention provides a method for determination of the solids weight fraction of a slurry comprising determining the concentration (wt/wt) of hydrogen in said slurry by neutron scatter or transmission measurement.

In one embodiment of the present invention said concentration is determined by a combination of neutron scatter or transmission measurement and at least one $\gamma$-ray scatter or transmission measurement.

It can be shown that the solids weight fraction $W_s$ of a coal slurry is related to hydrogen content (wt/wt) of the coal slurry, $H_{sl}$ and the coal, $H_c$, as follows:

$$W_s = \frac{\left(\frac{H}{W} - H_{sl}\right)}{\left(\frac{H}{W} - H_c\right)} \tag{1}$$

where (H/w) is the hydrogen content (wt/wt) of water which is approximately one-ninth. $H_{sl}$ can be accurately measured, as discussed hereafter. Hence, if $H_c$ is approximately constant, $W_s$ can be determined from a measurement of $H_{sl}$ alone. If, however, $H_c$ varies considerably due to changes in mineral matter concentration of the coal, then a further measurement(s) related to concentration of high atomic number constituents must be made so that $W_s$ can be accurately determined. This further measurement(s) must always be made if determination of mineral matter content is required. For slurries with solids other than coal, $H_c$ in equation (1) is replaced by the hydrogen content (wt/wt) of the solids.

The effect of change in concentration of mineral matter on accuracy of $W_s$ determination (i.e. without the further measurement(s) above) can be calculated. If the mineral matter concentration (wt/wt in coal) $C_{mm}$ changes to $C'_{mm}$, the corresponding new value of hydrogen concentration in the coal, $H'_c$, is given by:

$$H'_c = H_c \frac{(1 - C'_{mm})}{(1 - C_{mm})} \tag{2}$$

The error in $W_s$ determination caused by this change in $C_{mm}$ can be determined from equations (1) and (2). For example, if $W_s = 0.20$, $C_{mm} = 0.118$ and $C'_{mm} = 0.138$, the error in $W_s$ determination is 0.003188 (wt/wt). If an uncertainty of $\pm 0.01$ at a $W_s$ value of 0.20 can be tolerated, then a variation in concentration of mineral matter in the range ~0.06 to 0.18 is acceptable. This range is quite wide and hence the further measurement(s) will not be necessary for $W_s$ determination in many flotation streams of coal preparation plants.

Another cause of uncertainty in $H_c$ is the variation of hydrogen in the coal matter. For example, if $H_c$ changes from 0.04586 to 0.05, the corresponding error in determination of $W_s$ from equation (1) is $-0.01268$ at $W_s = 0.2$. It is not possible to correct for this variation by the further measurement(s) outlined above. Fortunately variations in $H_c$ are usually considerably less than from 0.04586 to 0.05 for coal from the same seam, and hence in practice the error in $W_s$ is significant but tolerable.

The accuracy to which $H_{sl}$ has to be measured to determine $W_s$ to within a specified error can also be calculated using equation (1). $H_c$ is assumed to be 0.04586, the mean for all coals whose composition is quoted in the Joint Coal Board and Queensland Coal Board pamphlet 'Eastern Australian Coals of Coking Potential', 1974. The calculation shows, for example, that to determine $W_s = 0.20$ to $\pm 0.01$, the relative error $(\Delta H_{sl}/H_{sl})$ in determining $H_{sl}$ must be no greater than 0.00665, i.e. 0.665% of $H_{sl}$.

Where hydrogen content is determined by a single neutron scatter or transmission measurement, the distance between the neutron source and the neutron detector should be carefully chosen so that the neutron measurement is insensitive to changes of hydrogen per unit volume but is sensitive to changes in hydrogen per unit weight.

Where hydrogen content is determined by combination of a neutron scatter or transmission measurement and a γ-ray scatter or transmission measurement, accuracy of determination of solids weight fraction is maintained over a wider range of $W_s$ compared with where the single neutron measurement is used. The distance between neutron source and detector is not critical within normal limits where sensitivity is sufficient for the measurement.

In cases where the accuracy of the determination of solids weight fraction is impaired by variation in mineral matter content of the coal in the slurry, compensation may be made by including an X-ray scatter or transmission measurement in the determination. In this case, mineral matter content of the coal can also be determined from a combination of the solids weight fraction of the slurry and the X-ray measurement.

The term "X-ray" when used in this specification and claims in relation to the method of the present invention is to be construed as including low energy γ-rays, i.e. those of such energy where absorption is atomic number dependent. The term γ-rays is used to describe γ-rays of such energy where absorption is substantially independent of atomic number of the sample under analysis.

If the higher atomic number constituents of the mineral matter in the coal (e.g., iron) are present to an appreciable concentration or where the concentration of those constituents varies substantially the accuracy of the determinations of solids weight fraction and mineral matter are less than for determinations where the concentration of those constituents is low and uniform. Compensation can be made in such cases by including a further X-ray transmission or scatter measurement at a different energy or by determining iron concentration, e.g. by X-ray fluorescence.

A promising method for determination of hydrogen (wt/wt) of the coal slurry is to use well-known techniques as follows:

(1) Neutron moderation to determine hydrogen per unit volume of slurry according to the method described in International Atomic Energy Agency, "Neutron Moisture Gauges", Technical Report Series No. 112, IAEA, Vienna, 1970, in Hall, A. W., Konchesky, J. L. and Stewart, R. F. "Continuous Monitoring of Coal by a Neutron Moisture Meter", U.S. Bureau of Mines Report of Investigations No. 7807 (1973), and in "Nuclear Assay of Coal Vol. 3: Determination of Total Hydrogen Content of Coal by Nuclear Techniques" Electric Power Research Institute (California, U.S.A.) Report EPRI FP-989 (1979) the disclosures of which are incorporated herein by reference. These techniques are based on use of a radioisotope source of fast neutrons such as $^{241}$Am/Be, $^{238}$Pu/Be, $^{252}$Cf, etc and a slow neutron detector such as $BF_3$ or $He_3$ proportional detectors or a scintillation detector. The references above relate to determination of moisture in soils and coal but not to slurries.

(2) γ-ray transmission or scatter to determine density of the coal slurry (i.e. mass of slurry per unit volume) (IAEA Technical Report Series No. 112 referred to above). γ-rays from radioisotope sources such as $^{137}$Cs, $^{133}$Ba, or $^{60}$Co are detected by scintillation detectors or ion chambers.

Promising methods giving a measurement relating to the concentration of the higher atomic number constituents are based on X-ray scatter or transmission. Preferred methods are:

3(a) For coal with iron content of the mineral matter low or varying within a limited range, a single measurement of X-ray transmission or scatter which gives a measurement related to the concentration of the higher atomic number constituents (i.e. ash constituents) in the coal. This measurement is described in Australian Pat. No. 501 427, the disclosure of which is incorporated herein by reference.

(b) For coal of higher and variable iron content either measurements of transmission or scatter by the coal slurry of X-rays at two separate energies or separate groups of energies, according to the method of Australian Pat. No. 501 427 or of Australian Patent Application No. PE 3079 or measurement of scatter of X-rays combined with a measurement of intensity of iron K X-rays excited in the coal, according to the method of Boyce, I. S., Clayton, C. G., and Page, D. "Some Considerations Relating to the Accuracy of Measuring the Ash Content of Coal by X-ray Backscattering", Nuclear Techniques and Mineral Resources 1977, IAEA, Vienna, 1977, pages 135–164, the disclosure of which is incorporated herein by reference.

A simple case for determination of solids weight fraction of the coal slurry containing entrained air (voidage) is for slurries containing coal with mineral matter content varying in a restricted range as discussed hereinabove. In this case, combination of (1) and (2) above gives $W_s$. In a special example of this case a neutron measurement alone is sufficient to determine hydrogen per unit weight of coal slurries and hence solids weight fraction. In this example, the neutron source and detector are spaced apart at a distance where the neutron count rate is essentially independent of hydrogen per unit volume of slurry over a limited range of slurry densities (see discussion in relation to FIG. 3 in the previously quoted reference by Hall et al).

If the mineral matter content varies over a wide range, then (1) and (2) must be combined with 3(a) or 3(b) to give solids weight fraction with greater accuracy.

In all the above cases, solids weight fraction is determined independent of voidage in the slurry assuming voids are distributed relatively uniformly throughout the slurry. In the last case (1, 2 and 3(a) or 3(b) combined), mineral matter content is also determined independent of voidage in the slurry. Where neutron measurement alone is used to determine solids weight fraction of the slurry, it can be combined with scatter of X-rays with or without iron K X-ray intensity (depending on whether the range of iron concentrations in the ash are large or limited) to give solids weight fraction and mineral matter content independent of voidage.

The combination of neutron, $\gamma$- and X-ray measurements to determine mineral matter content and solids weight fraction is illustrated by the following example. Consider the neutron measurement determining hydrogen per unit volume of slurry, and $\gamma$-ray transmission measurement determining the product $\rho x$ where $\rho$ is the density of the slurry containing voidage and $x$ is the path length traversed by the $\gamma$-rays in the slurry. Assume that a collimated beam of low energy $\gamma$-rays traversed the same path as the higher energy $\gamma$-rays. The intensity of detected low energy $\gamma$-rays I detected with slurry present is related to the intensity of detected $\gamma$-rays with no slurry present $I_o$ by:

$$(I/I_o) = \exp(-\mu_{sl}\rho x) \qquad (3)$$

where $$\mu_{sl} = \{\mu_{cm} + (\mu_{mm} - \mu_{cm})C_{mm}\}W_s + \mu_{H2O}(1 - W_s) \qquad (4)$$

and subscripted values of $\mu$ are the narrow beam mass absorption coefficients of the low energy $\gamma$-rays and subscripts cm, mm, sl and H2O refer respectively to coal matter, mineral matter, slurry and water. Since $\rho x$ is determined by the (higher energy) $\gamma$-ray measurement, $\mu_{sl}$ is determined by the low energy $\gamma$-ray measurement. $\mu_{cm}$, $\mu_{mm}$ and $\mu_{H2O}$ are determined from tabulated mass absorption coefficients and typical elemental composition of coal for the particular application. Equations (1) and (4) are now combined, replacing $H_c$ in equation (1) by $H_{cm}(1-C_{mm})$ where $H_{cm}$ is the hydrogen content (wt/wt) in the coal matter. From equations (1) and (4).

$$C_{mm} = \left\{ \frac{\left(\frac{H}{W} - H_{cm}\right)}{\left(\frac{H}{W} - H_{sl}\right)} - \frac{(\mu_{cm} - \mu_{H2O})}{(\mu_{sl} - \mu_{H2O})} \right\} \bigg/ \left\{ \frac{(\mu_{mm} - \mu_{cm})}{(\mu_{sl} - \mu_{H2O})} - \frac{H_{cm}}{\left(\frac{H}{W} - H_{sl}\right)} \right\} \qquad (5)$$

and $$W_s = \frac{\left(\frac{H}{W} - H_{sl}\right)}{\left(\frac{H}{W} - H_{cm}(1 - C_{mm})\right)} \qquad (6)$$

Hence both solids weight fraction and mineral matter content can be determined from measurements of $H_{sl}$ and high and low energy $\gamma$-ray transmission. The accuracy of determination of $W_s$ and $C_{mm}$ can be determined from the above equations and knowledge of typical variations in chemical composition of the coal. If the iron concentration of the mineral matter varies considerably, then $\mu_{mm}$ cannot be assumed essentially constant, and the measurements 3(b) must be used instead of the single low energy $\gamma$-ray transmission or scatter.

The solids weight fraction is derived from hydrogen (wt/wt) which includes a neutron measurement. If coal contains varying concentrations of elements of high neutron cross-section, this would depress the neutron flux in the slurry and hence introduce errors in determination of solids weight fraction. Calculations based on thermal neutron cross-sections and concentrations of elements in coal show that, for coal slurries, the absorption by elements (other than hydrogen) in the coal is very small compared with the absorption by hydrogen (in water and in coal). Hence the error introduced in the determination of solids weight fraction is negligible. For slurries with solids other than coal, the accuracy of determination of solids weight fraction also depends on neutron flux depression due to chemical composition of the solids. The determination is accurate when the change in thermal neutron cross-section of solids (due to changes in chemical composition) is very small compared to the total neutron cross-section of the slurry.

A first preferred form of the invention comprises either a neutron measurement alone with careful choice of source to detector separation or a combination of a neutron backscatter or transmission measurement by the slurry and $\gamma$-ray backscatter or transmission measurement by the slurry. This form determines solids weight fraction of the slurry where the coal under analysis has a mineral matter content which varies in a restricted range.

A second preferred form of the invention provides a method for determination of the solids weight fraction of a coal slurry and the mineral matter content of the coal in said slurry by a combination of a first measurement comprising a combination of neutron backscatter or transmission of said slurry and $\gamma$-ray scatter or transmission of said slurry and a second measurement which is either (a) X-ray scatter or transmission or (b) either a measurement of scatter of X-rays combined with a measurement of intensity of iron K X-rays or measurements of transmission or scatter by the coal slurry of low energy $\gamma$-rays or X-rays at two separate energies or separate groups of energies. This second form of the invention determines solids weight fraction even though mineral matter content of the coal varies over a very wide range. It also determines mineral matter content.

A third preferred form of the invention is a neutron measurement with careful choice of source to detector separation combined with scatter of X-rays and, if necessary, iron K X-ray intensity. This form of the invention determines both solids weight fraction and mineral matter content of the coal slurry.

Preferred embodiments of the invention are described with reference to the accompanying drawings in which:

FIG. 1 represents probes immersed in a coal slurry stream; and

FIG. 2 represents a different type of neutron probe to that shown in FIG. 1.

FIG. 3 represents probes mounted on a pipeline.

It is emphasised that X-ray scatter and transmission each give a determination of X-ray absorption in the coal slurry and hence are usually interchangeable. X-ray transmission includes not only direct transmission but also scatter-transmission.

Probes immersed into the coal slurry

EXAMPLE 1

Probes immersed directly into coal slurry streams are shown in FIG. 1. Coal slurry in pipe 1 flows into a "box" 2 containing baffle plates 3, density probe 4, neutron backscatter probe 5 and agitator 6 before overflowing into a sump 7. The baffle plates help to reduce the content of air entrained in the slurry prior to entering the "analysis zone" containing the immersed probes, and the agitator helps produce a uniform coal slurry over the entire analysis zone.

The density probe 4 consists of two pats 8 and 9 held together with rods 10 so that coal slurry flows between 8 and 9. The lower part 8 consists of a shield and collimator 11 and a radioisotope γ-ray source 12. The top part 9 contains a scintillation detector 13 and a collimator 14. The shields, radioisotope source, collimators and detector are arranged so that a narrow beam of γ-rays is transmitted through the coal slurry to the detector. The electronics associated with the probe are conventional, including amplifier, gain stabiliser, single channel analyser, interface and digital computer or microprocessor.

The X-ray or low energy γ-ray probe 15 consists of two parts 16 and 17 held together by rods 18 so that coal slurry flows between 16 and 17. The lower part 16 consists of a shield and collimator 19 and a radioisotope X-ray or low energy γ-ray source 20. The top part 17 contains a scintillation detector 21 and a collimator 22. The shields, radioisotope source, collimators and detector are arranged so that a narrow beam of X-rays or low energy X-rays is transmitted through the coal slurry to the detector. The electronics associated with the probe are similar to those used with the density probe. This X-ray probe is not necessary for the determination of solids weight fractions if the mineral matter content of the coal varies over only a narrow range. It is, however, necessary if the mineral matter content is to be determined.

The neutron backscatter probe 5 contains a radioisotope neutron source 23 and slow neutron detector 24. Electrical pulses from this detector are routed to an amplifier, gain stabiliser, single channel analyser, interface, and digital computer or microprocessor. Another type of neutron probe 25 shown in FIG. 2, has the neutron source 23 well separated from the slow neutron detector 24. The space between source and detector in this probe may be empty or open to the slurry or may contain shielding material. This geometry ensures that neutrons have traversed considerable distance in the slurry before detection. The slow neutron detector in both neutron probes are well-established detectors such as proportional counters with $^3$He or $BF_3$ gas, or a scintillation detector such as LiI or lithium glass.

The computer or microprocessor outputs the solids weight fraction and mineral matter content of the coal slurry. This measurement is independent of voidage of the slurry assuming the voidage is essentially constant over analysis volumes of the density, X-ray and neutron probes.

If iron content of coal in the slurry varies considerably, the X-ray probe (FIG. 1) would be replaced by another type of X-ray probe. This latter probe would have a thin window isolating radioisotope X-ray source and detector from the slurry but which transmits X-rays scattered by the slurry and iron K X-rays excited in the slurry. The scattered X-rays and iron K X-rays detected would be separated by pulse height selection using conventional electronics, and combined with the γ-rays and neutron measurements from the other probes to give the solids weight fraction. The detector in this case would be a scintillation detector (particularly for slurries with a high solids weight fraction), or a proportional detector, or a solid state detector (either ambient temperature, or cooled by liquid nitrogen or thermoelectrically cooled).

In this preferred embodiment, it will in some cases be possible to replace the high energy and low energy γ-ray probes by a single probe and using energy analysis to separate the intensities of the high and low energy γ-rays.

(b) EXAMPLE 2

Two probes would be immersed in the coal slurry:

(i) A neutron probe as in FIG. 2 with the distance between source and detector carefully chosen so that the neutron measurement is insensitive to changes of hydrogen per unit volume but is sensitive to changes in hydrogen per unit weight.

(ii) The X-ray scatter probe described in the second last paragraph of Example 1.

Signals from the probes are amplified and processed by conventional electronics including a digital computer or microprocessor to give an output of solids weight fraction and content of mineral matter.

Probes mounted about pipelines

EXAMPLE 3

Probes mounted about a pipeline are shown in FIG. 3.

Coal slurry 26 flows through a pipeline 27 about which the radioisotope gauges are mounted. X-rays from X-ray source 28 are collimated by shields 29 to ensure that a narrow beam of X-rays are detected by detector 30. Windows 31 of low atomic number material are fitted to the pipeline to ensure transmission of X-rays to the detector 30.

γ-rays from γ-ray source 32 are collimated by shields 29 to ensure that a narrow beam of γ-rays are detected by detector 33. Windows are not normally required for a γ-ray gauge.

In some applications, the X-ray gauge and γ-ray gauge may be combined such that the source emits both X- and γ-radiation and, following detection, the X- and γ-rays are separated by pulse height analysis.

The neutron backscatter gauge is mounted on one side of the pipeline with radioisotope neutron source 34 and slow neutron detector 35 as shown. It is also possible to use a neutron transmission gauge. The electronics for all three gauges are similar to that described in relation to FIG. 1.

What I claim is:

1. A method for determination of the solids weight fraction of a slurry comprising determining the relative concentration of hydrogen by weight in said slurry by neutron scatter or transmission measurement, and calculating the solids weight fraction from said concentration of hydrogen.

2. A method as defined in claim 1 wherein said concentration is determined by a combination of neutron scatter or transmission measurement and a γ-ray scatter or transmission measurement.

3. A method as defined in claim 1 wherein said slurry is a coal slurry.

4. A method as defined in claim 3 wherein said concentration is determined by a combination of a neutron scatter or transmission measurement and at least one X-ray scatter or transmission measurement.

5. A method as defined in claim 3 wherein said concentration is determined by a combination of neutron scatter or transmission measurement, an γ-ray scatter or transmission measurement and an X-ray scatter or transmission measurement.

6. A method as defined in claim 4 or 5 wherein at least two X-ray scatter or transmission measurements are made.

7. A method as defined in claim 6 wherein said iron concentration is measured by X-ray fluorescence.

8. A method as defined in claim 4 or 5 further comprising determining the mineral matter content of the coal in said slurry wherein said mineral matter content is calculated from said relative weight concentration of hydrogen and said at least one X-ray scatter or transmission measurement.

9. A method as defined in claim 3, 4 or 5 wherein at least one of said solids weight fraction and said mineral matter content is determined by at least one probe immersed into said slurry.

10. A method as defined in claim 3, 4 or 5 wherein at least one of said solids weight fraction and said mineral matter content is determined by at least one probe mounted about a pipeline which carriers said slurry.

11. A method as defined in claim 4 or 5 wherein a first plurality of measurements are made for a second plurality of energy levels or groups of energy levels, and at least one measurement is made for each of said energy levels or groups of energy levels, and each of said levels or groups of energy levels is measured at least once.

12. A method as defined in claim 4 or 5, wherein a measurement is made of the iron present in the slurry.

13. A method as defined in claim 12 further comprising determining the mineral matter content of the coal in said slurry wherein said mineral matter content is calculated from said relative weight concentration of hydrogen and said at least one X-ray scatter or transmission measurement combined with said measurement of iron concentration.

14. A method as defined in claim 4 or 5, further comprising determining the mineral matter content of the coal in said slurry wherein said mineral matter content is calculated from said relative weight concentration of hydrogen and said at least one X-ray scatter or transmission measurement.

* * * * *